United States Patent
Himeno

(10) Patent No.: US 11,875,106 B2
(45) Date of Patent: Jan. 16, 2024

(54) DOCUMENT CREATION SYSTEM

(71) Applicant: IRYOU JYOUHOU GIJYUTU KENKYUSHO CORPORATION, Fukuoka (JP)

(72) Inventor: Shinkichi Himeno, Fukuoka (JP)

(73) Assignee: IRYOU JYOUHOU GIJYUTU KENKYUSHO CORPORATION, Fukuoka (JP)

( * ) Notice: Subject to any disclaimer, the term of this patent is extended or adjusted under 35 U.S.C. 154(b) by 0 days.

(21) Appl. No.: 17/672,324

(22) Filed: Feb. 15, 2022

(65) Prior Publication Data

US 2022/0180046 A1 Jun. 9, 2022

Related U.S. Application Data

(63) Continuation-in-part of application No. PCT/JP2020/035168, filed on Sep. 17, 2020.

(30) Foreign Application Priority Data

Sep. 26, 2019 (JP) ................................. 2019-176055

(51) Int. Cl.
*G06F 40/166* (2020.01)
*G16H 10/00* (2018.01)
*G06F 40/134* (2020.01)

(52) U.S. Cl.
CPC .......... *G06F 40/166* (2020.01); *G06F 40/134* (2020.01); *G16H 10/00* (2018.01)

(58) Field of Classification Search
None
See application file for complete search history.

(56) References Cited

U.S. PATENT DOCUMENTS

| | | | | |
|---|---|---|---|---|
| 5,696,885 A | * | 12/1997 | Hekmatpour | G06F 3/0481 706/59 |
| 5,878,423 A | * | 3/1999 | Anderson | G06F 16/907 707/999.102 |
| 6,023,715 A | * | 2/2000 | Burkes | G06F 40/131 715/207 |

(Continued)

FOREIGN PATENT DOCUMENTS

| JP | H3-51951 A | 3/1991 |
|---|---|---|
| JP | 2004-139312 A | 5/2004 |

(Continued)

OTHER PUBLICATIONS

Demeulemeester et al. "Clinical pathways and operations management: it takes two to tango." Tijdschrift voor Economie en Management 3 (2007), pp. 451-469.*

(Continued)

*Primary Examiner* — Maikhanh Nguyen
(74) *Attorney, Agent, or Firm* — Maier & Maier, PLLC

(57) ABSTRACT

A document creation system includes a term object creation configured to create term objects in which terms and attributes thereof are integrated, a term object management configured to record and manage the created term objects, a term object selection configured to select a necessary term object from among the term objects managed in the term object management, and a term object placement configured to place the selected term object in a document being edited.

7 Claims, 4 Drawing Sheets

(56) References Cited

U.S. PATENT DOCUMENTS

| | | | | |
|---|---|---|---|---|
| 7,716,072 | B1* | 5/2010 | Green, Jr. | G16H 10/60 |
| | | | | 705/3 |
| 8,595,620 | B2* | 11/2013 | Larsen | G16H 10/60 |
| | | | | 715/254 |
| 10,437,962 | B2* | 10/2019 | Soni | G16H 20/10 |
| 11,410,650 | B1* | 8/2022 | Agassi | G06V 40/20 |
| 11,605,005 | B2* | 3/2023 | Himeno | G06F 16/9024 |
| 2004/0039628 | A1* | 2/2004 | Thompson | G06Q 10/0639 |
| | | | | 705/7.14 |
| 2004/0078241 | A1 | 4/2004 | Shiobara | |
| 2005/0228688 | A1* | 10/2005 | Visser | G06Q 30/018 |
| | | | | 705/317 |
| 2006/0116908 | A1* | 6/2006 | Dew | G16H 10/60 |
| | | | | 705/2 |
| 2008/0320412 | A1* | 12/2008 | Wake | G06F 3/0486 |
| | | | | 715/781 |
| 2009/0249180 | A1* | 10/2009 | Cheng | G06F 40/103 |
| | | | | 715/256 |
| 2010/0066691 | A1 | 3/2010 | Li | |
| 2011/0078570 | A1* | 3/2011 | Larsen | G16H 10/60 |
| | | | | 715/710 |
| 2011/0178820 | A1* | 7/2011 | Soni | G16H 20/10 |
| | | | | 705/3 |
| 2013/0246098 | A1* | 9/2013 | Habboush | G06Q 10/10 |
| | | | | 705/3 |
| 2013/0297348 | A1* | 11/2013 | Cardoza | G16H 40/20 |
| | | | | 705/3 |
| 2013/0346106 | A1* | 12/2013 | Xiao | G06Q 10/10 |
| | | | | 705/3 |
| 2015/0356057 | A1* | 12/2015 | Subramanian | G06F 40/10 |
| | | | | 704/9 |
| 2015/0356198 | A1 | 12/2015 | D'Souza et al. | |
| 2015/0356646 | A1* | 12/2015 | Spitznagel | G16H 40/20 |
| | | | | 705/2 |
| 2015/0356647 | A1* | 12/2015 | Reiser | G06Q 30/04 |
| | | | | 705/3 |
| 2018/0218786 | A1* | 8/2018 | Himeno | G06F 21/31 |
| 2020/0320405 | A1 | 10/2020 | Himeno | |

FOREIGN PATENT DOCUMENTS

| | | |
|---|---|---|
| JP | 2010-073185 A | 4/2010 |
| JP | 4477994 B2 | 6/2010 |
| JP | 6485164 B2 | 3/2019 |
| JP | 2019-101517 A | 6/2019 |

OTHER PUBLICATIONS

J. Cheah, "Clinical pathways—an evaluation of its impact on the quality care in an acute care general hospital in Singapore." Singapore medical journal 41.7 (2000), pp. 335-346.*

International Search Report dated Dec. 1, 2020, in corresponding to International Application No. PCT/JP2020/035168; 5 pages (with English Translation).

Japanese Office Action dated Mar. 6, 2020, in corresponding to Japanese Patent Application No. 2019-176055; 12 pages (with English Translation).

Kouji Kozaki; "Domain Ontology Developments and their Utilization"; Institute of Science and Industrial Research; Journal of Japan Society of Information and Knowledge; Feb. 15, 2010; vol. 19; No. 4; pp. 296-305; ISSN0917-1436.

European Search Report, dated Oct. 13, 2022, in corresponding International Patent Application No. PCT/JP2020/035168; 8 pages.

* cited by examiner

SECOND EXAMPLE TERM OBJECT

| TERM | BODY TEMPERATURE (FREELY INPUTTED VALUE) | CLASS | | FEVER TYPE | TEXT COMMENT (FREELY INPUTTED) |
|---|---|---|---|---|---|
| BODY TEMPERATURE | 38.2 (°C) | 0 : | <37°C | NORMAL TEMPERATURE | CONTINUED FEVER |
| | | 1 : | 37.0 TO 37.5 | SLIGHT FEVER | REMITTENT FEVER |
| | | 2 : | 37.5 TO 38°C | MODERATE FEVER | INTERMITTENT FEVER |
| | | 3 : | 38°C OR MORE | HIGH FEVER | RECURRENT FEVER |
| | | | | | UNDULANT FEVER |

ATTRIBUTES

DOCUMENT CREATION SYSTEM

TECHNICAL FIELD

The present invention relates to a document creation system that makes standardized descriptions having no fluctuation by converting terms used to create documents, into objects, as well as automatically makes logic judgements and automatically creates indexes by embedding scripts to be executed with respect to the terms and providing reference links between the term objects and the documents or cases to which the documents belong.

BACKGROUND

In medical sites and the like, it has become common to use a PC to create a medical document (electronic health record). Doctor or nurse records, test or treatment instructions (orders), and the like are being digitized. Attempts are being made to analyze medical care or caregiving using the accumulated great amount of electronic data (big data) and to improve the treatment method.

Background art literature relating to the present application includes the following.

CITATION LIST

Patent Literature

Patent Literature 1: Japanese Patent No. 6485164
Patent Literature 2: Japanese Patent No. 4477994

SUMMARY

When the patient state or the like is described in a free style, the terms or the expression of degree thereof fluctuate, for example, as seen in fever, high fever, slight fever, or −, +−, ++, or 0 to 5 degrees, or the like.

When an attempt is made to perform statistical processing later, it is difficult to compile similar descriptions as the same items.

For example, when a list of cases (electronic health records) in which fever symptoms have been observed is required, searching for documents or the like describing the cases one by one takes an enormous amount of time and is impractical. It is necessary to previously construct a general-purpose index.

There is also a method of limiting terms for description using a controlled vocabulary (thesaurus).

However, for example, when prescribing a drug, it is required to describe not only terms but also the number of tablets per day, the dosage frequency, the dosage timing, and the like in a predetermined format.

Also, it is often required to make checks such as whether a disease name corresponding to the drug involved has already been registered in the case involved or whether a reduction in hepatic or renal function is not a contraindication to the drug.

As seen above, simply using a dictionary such as a thesaurus is not sufficient in controlling terms.

There are many terms having common attributes. When all attributes are repeatedly recorded, the recording capacity is increased. Also, when a change has to be made to one attribute, changes have to be made to all the common attributes repeatedly, resulting in an enormous amount of maintenance work.

An enumeration of only terms in a controlled vocabulary makes the document less readable.

A form in which terms in a controlled vocabulary are embedded in a natural sentence is preferable.

Use of term objects in which various attributes are integrated with terms in a controlled vocabulary may enormously increase the recording capacity of a created document.

At medical sites, clinical pathways in which tests or treatment to be conducted for each disease are developed on a time axis are being used.

There are medical institutions using more than 1000 clinical pathways. For those medical institutions, it is hard work to change (update) the specifications of the tests or treatment embedded in the clinical pathways. Mistakes often occur in such work.

The present invention has been made to solve the above problems with the background art, and an object thereof is to provide a document creation system having high functionality and excellent maintenability that creates easy-to-read documents having no fluctuations in expression or format by converting many terms used in the documents and the attributes thereof into objects and placing, in the documents, term objects selected from a list in which the term objects are managed, automatically creates an index from the placed term objects to the documents or cases to which the documents belong so that searches can be performed later, by creating reference links from the term objects to the documents or cases, semi-automatically improves safety by embedding scripts to be checked for execution in the attributes of the term objects, provides term object management means that has a small recording capacity, shows good visibility, and has excellent maintainability, by pulling out the common attributes of the term objects into parent term objects and thus forming a parent-child tree structure, allows a great amount of documents to be recorded with a small recording capacity by providing means that converts an already edited document including a term object into plain text and restores the document including the term object when necessary, and facilitates the update of a test or treatment embedded in a clinical pathway.

As means for accomplishing the object, a document creation system includes term object creation means configured to create term objects in which terms and attributes thereof are integrated, term object management means configured to record and manage the created term objects, term object selection means configured to select a necessary term object from among the term objects managed in the term object management means, and term object placement means configured to place the selected term object in a document being edited.

According to the document creation system, the term object management means includes reference link means configured to link the term object placed in the document to at least one of (i) the document or (ii) a case to which the document belongs.

The document creation system includes script incorporation means configured to record, in the term object, a script describing an operation to be performed.

According to the document creation system, the document creation system includes comment incorporation means configured to record, in the term object, a freely described comment to be displayed in the document.

According to the document creation system, the document creation includes term object attribute inheritance means configured to organize the term objects into a tree using parent-child relationships in contents between the term objects and to cause child term objects to inherit attributes of parent term objects as attributes of the child term objects.

According to the document creation system, the document creation includes term object-to-plain text conversion means configured to convert the document having the term object placed therein into plain text from which an object element has been removed so that a recording capacity of the document can be reduced.

According to the document creation system, the document creation system includes plain text-to-term object conversion means configured to restore the document converted into the plain text to the document having the term object placed therein.

According to the document creation system, the document creation system includes schedule creation means configured to implement, in a schedule in which matters to be executed to achieve a particular purpose are developed on a time axis, the matters to be executed using the term objects.

According to the document creation system, the document creation system includes in-schedule particular term object list display means configured to, when changes are made to particular term objects in the schedule creation means, display a list of positions in which the particular term objects are present.

According to the document creation system, the document creation system includes in-schedule particular term object update means configured to update the term objects in the schedule using the changed term objects in the in-schedule particular term object list display means.

The document creation system of includes the term object creation means and thus creates term objects in which terms and attributes thereof are integrated.

The document creation system includes the term object management means and thus records and manages the created term objects.

The document creation system includes the term object selection means and thus selects a necessary term object from among the term objects managed in the term object management means.

The document creation system includes the term object placement means and thus places the selected term object in a document being edited.

In the document creation system, the term object management means includes reference link means configured to link the term object placed in the document to at least one of (i) the document or (ii) a case to which the document belongs.

The document creation system includes the script incorporation means and thus records, in the term object, a script describing an operation to be performed.

The document creation system includes the comment incorporation means and thus records, in the term object, a freely described comment to be displayed in the document.

The document creation system includes the term object attribute inheritance means and thus organizes the term objects into a tree using parent-child relationships in contents between the term objects and causes child term objects to inherit attributes of parent term objects as attributes of the child term objects.

The document creation system includes the term object-to-plain text conversion means and thus converts the document having the term object placed therein into plain text from which an object element has been removed so that a recording capacity of the document can be reduced.

The document creation system includes plain text-to-term object conversion means and thus restores the document converted into the plain text to the document having the term object placed therein.

The document creation system includes the schedule creation means and thus implements, in a schedule in which matters to be executed to achieve a particular purpose are developed on a time axis, the matters to be executed using the term objects.

The document creation system includes the in-schedule particular term object list display means and thus, when changes are made to particular term objects in the schedule creation means, displays a list of positions in which the particular term objects are present.

The document creation system includes the in-schedule particular term object update means and thus updates the term objects in the schedule using the changed term objects in the in-schedule particular term object list display means.

DETAILED DESCRIPTION

The present application is a system that is run using a computer.

This computer includes an input device (mouse, keyboard, etc.), an output device (monitor, printer, etc.), a storage device (memory, hard disk), a computing device (CPU), a controller (CPU), and the like, as well as includes a program for performing the means (functions) of the present application.

The document creation system includes the server apparatus, the database and the terminal. The server apparatus, the database and the terminal connected through network.

The server apparatus is a prior computer. The server apparatus includes: an arithmetic apparatus including the processor, a main storage apparatus, an auxiliary storage apparatus, input apparatus, output apparatus, and communication apparatus. The arithmetic apparatus, the main storage apparatus, the auxiliary storage apparatus, input apparatus, output apparatus, the communication apparatus connected through a bus interface. The arithmetic apparatus includes the processor that can execute an instruction set. The main storage apparatus includes a volatile memory such as a random access memory (RAM). The auxiliary storage apparatus includes a recording medium such as a nonvolatile memory, and a recording method thereof is not limited. The recording medium indicates a hard disk drive (HDD) or a solid state drive (SSD), for example. The input apparatus is, for example, a keyboard device. The output apparatus includes, for example, display as a liquid crystal panel. The communication apparatus is a network interface that can connect to network. The processor of the server apparatus executes the function of the units of the document creation system including: a term object creation means, a term object management means, a term object selection means, a term object placement means or the like. The database is composed of the auxiliary storage apparatus of the server apparatus or the auxiliary storage apparatus independent from the server apparatus. The database stores information managed by the document creation system. The terminal is a prior computer including a processor.

Figure 1:
FIG. 1 shows an example term object of the present invention.

FIG. 1 shows an example term object of the present invention.

A drug "Loxonin tablets" is used as a term.

Shown as attributes are attribute items such as the number (1 to 6) of tablets to be prescribed, the number (1× or greater) of division of the prescribed tablets, the usage/dosage including the dose timing (as needed, after breakfast, etc.), the number of prescription days, (freely inputted) comment text, and a script recording matters to be conducted when making a prescription.

With respect to the usage/dosage, the number of prescription days, and the like, a format used to input those items to medical fee billing software is precisely set. For this reason, if those items are freely described, such descriptions are difficult to input.

It is essential to control the format so that descriptions are always inputted, as shown in FIG. 1.

The format is precisely controlled, for example, by previously converting terms into objects, placing the objects in a document, then clicking each attribute item to develop a pulldown menu, and selecting any item.

It is also important to change the development range (for example, when the number of tablets is 2, the number of division cannot be 3× or greater) of the subsequent attribute item on the basis of the selection in the preceding attribute item.

Pieces of information that cannot be expressed in the precise format described together in text in the comment attribute item.

Figure 2:
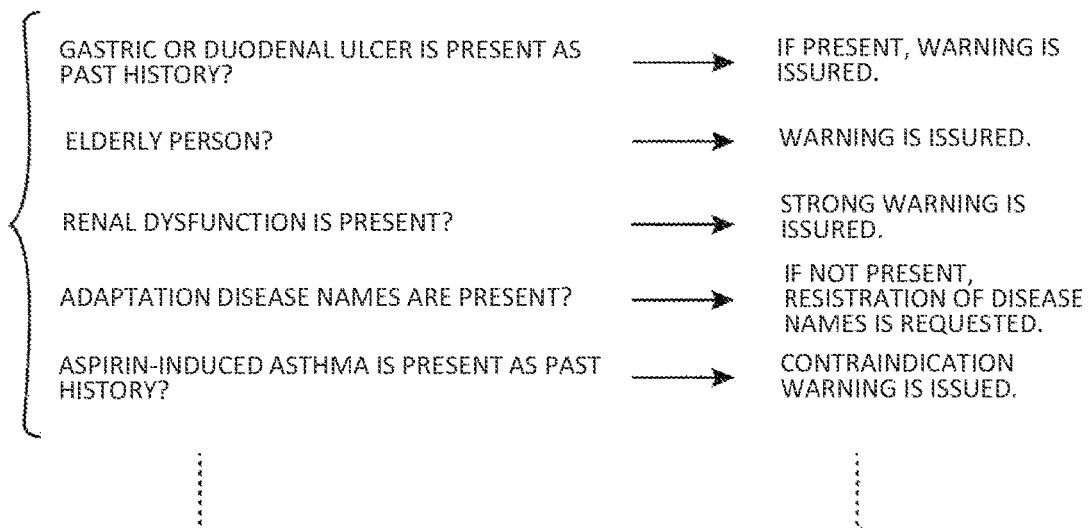
FIG. 2 shows an example of descriptions in the script attribute item of the term object of FIG. 1.

FIG. 2 shows an example of descriptions in the script attribute item of the term object of FIG. 1.

To actually formulate a drug on the basis of a prescription document and pass the drug to the patient, it is necessary to perform various prior checks on medical safety.

With respect to "gastric or duodenal ulcer is present as a past history?", which is included in the example, the case document (health record) of the patient involved is searched for in the electronic health record. If present, the prescription doctor needs to be warned on the prescription screen due to a risk that the drug may revive or exacerbate the gastric or duodenal ulcer.

Also, elderly persons are more likely to have side effects. In particular, the drug is dangerous for elderly persons having renal dysfunction.

The age and data on renal function tests are searched for in the electronic health record. If applicable, the prescription doctor needs to be urged to reconsider the prescription of the drug on the prescription screen.

Also, a search is performed as to whether the adaptation disease names of the drug (the disease names with respect to which the drug is allowed to be prescribed) are registered in the electronic health record. If not yet, a list of the adaptation disease names is displayed and the prescription doctor is urged to register the disease names in the case document (health record).

If aspirin-induced asthma is present as a past history, the prescription doctor is warned that aspirin-induced asthma contraindicates the drug.

Doing so can reduce the risk that the patient may take this drug and then have side effects.

Also, by preventing registration omission of the disease names, an assessment (payment refusal) after billing for the medical fee can be prevented.

Note that in FIG. 2, the timing when the script is executed is when the entire prescription document is confirmed or when a temporary execution command is issued before the confirmation. However, although not shown, the execution timing may be changed to when a person of an occupation other than doctor refers to the document or other timings, depending on the document type or the term object. For this reason, means for registering the execution timing may be provided.

The script may be implemented using any method. One example method is to describe the script in a script language. Another example method includes previously registering many execution modules described in JavaScript, PYTHON, or the like and specifying a necessary execution module (script incorporation means).

Figures 3, 4:
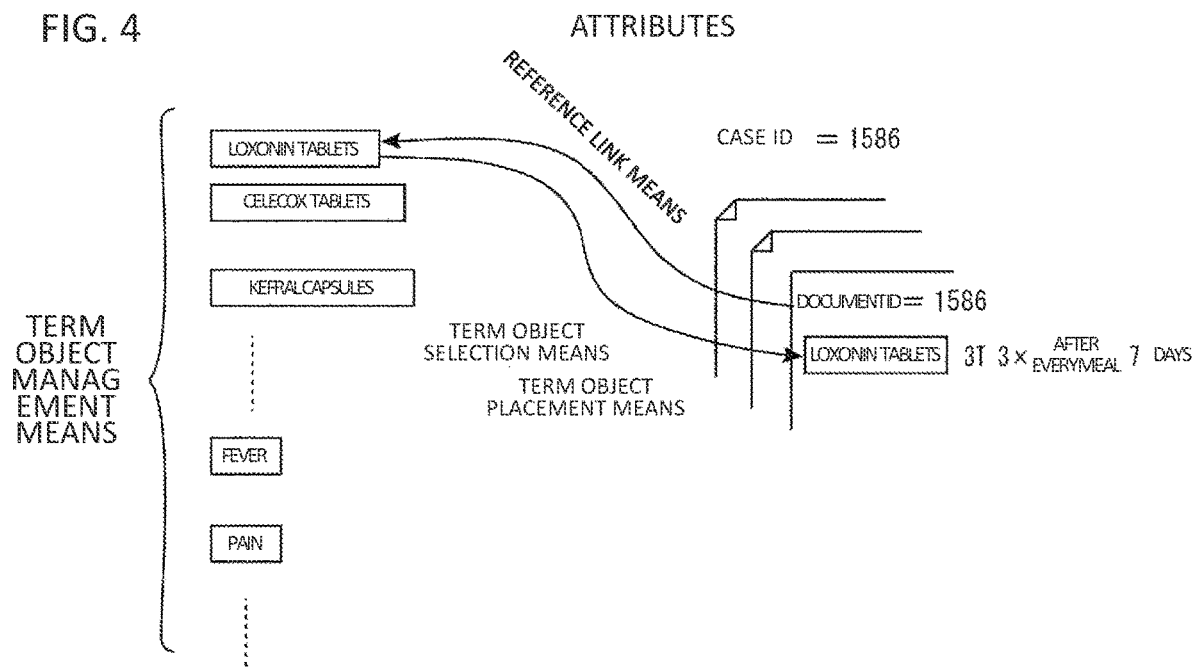
FIG. 3 shows another example term object of the present invention.
FIG. 4 is a diagram showing that a necessary term object is selected from term objects managed in term object management means (term object selection means) and placed in a document (term object placement means) and at least one of the document ID of the document and the ID of a case including the document is registered as a reference link in the term object in the term object management means (reference link means).

FIG. 3 shows another example term object of the present invention.

This term object is formed by setting attribute items such that fluctuations in the terms or description omission do not occur in a document in which a doctor or the like describes the symptoms or findings of a patient and the description can be statistically analyzed later.

With reference to the term "body temperature," the value of the body temperature (38.2 (° C.) in this example) is freely inputted, and a class "3 high temperature" is assigned to the value on the basis of a classification criterion.

The fever type is selected from a list, and comment text is allowed to be freely inputted when necessary.

An enumeration of expressions such as "body temperature 38.2° C.," "high fever," and "remittent fever" makes the health record document less readable. For this reason, it is also useful to embed the term object in a natural sentence "body temperature 38.2° C., high fever, and remittent fever, but does not look so tough" by freely inputting comment text.

FIG. 4 is a diagram showing that a necessary term object is selected from term objects managed in term object management means (term object selection means) and placed in a document (term object placement means) and at least one of the document ID of the document and the ID of a case including the document is registered as a reference link in the term object in the term object management means (reference link means).

The term object management means manages the term objects in which terms and attributes thereof are integrated, as a list.

The term objects include prescription term objects whose format has to be precisely managed, such as drug names and blood test names, and description term objects used to describe symptoms or findings. A list of the prescription term objects and a list of the description term objects may be managed together as shown in FIG. 4, or may be managed separately.

The term object selection means and term object placement means highlights a proper term object among the listed term objects and drag and drop the term object to a specified position of a document being edited and thus embed it therein.

The highlighting and dragging/dropping operations may be performed using a mouse, or may be performed using a fingertip on a touchscreen.

Arrow buttons on a keyboard or a cursor may be used.

Or a method may be used including inputting a term to the specified position of the document using the keyboard or the like, searching for and selecting a term object corresponding to the term in the term object management means, and embedding the term object in the document.

Simultaneously, the term object placed in the document is recorded in the term object in the term object management means using, as reference link means, at least one of the document ID of the document (a record number or the like on a document database recording all documents of all cases and the ID of a case to which the document belongs (health record number, etc.).

Thus, a list of cases or documents in which this object is placed is easily obtained. While searching for a case only requires a case ID, searching for a document in the case requires also a document ID.

Figure 5:
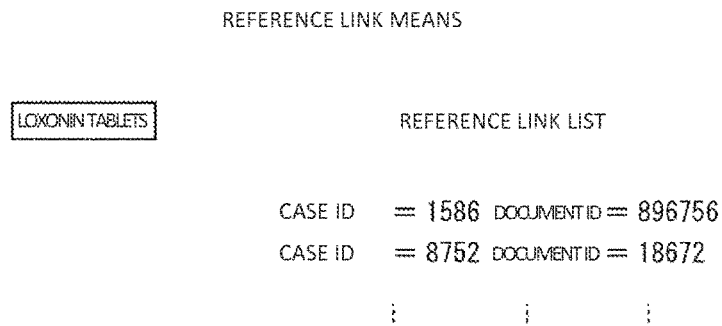
FIG. 5 is a diagram showing a list of reference links registered in the term object in the term object management means shown in FIG. 4.

FIG. 5 is a diagram showing the reference link list of the reference link means registered in the term object in the term object management means shown in FIG. 4.

In FIG. 5, the term object is recording the case IDs and document IDs of the documents in which the term object is placed.

Figure 6:
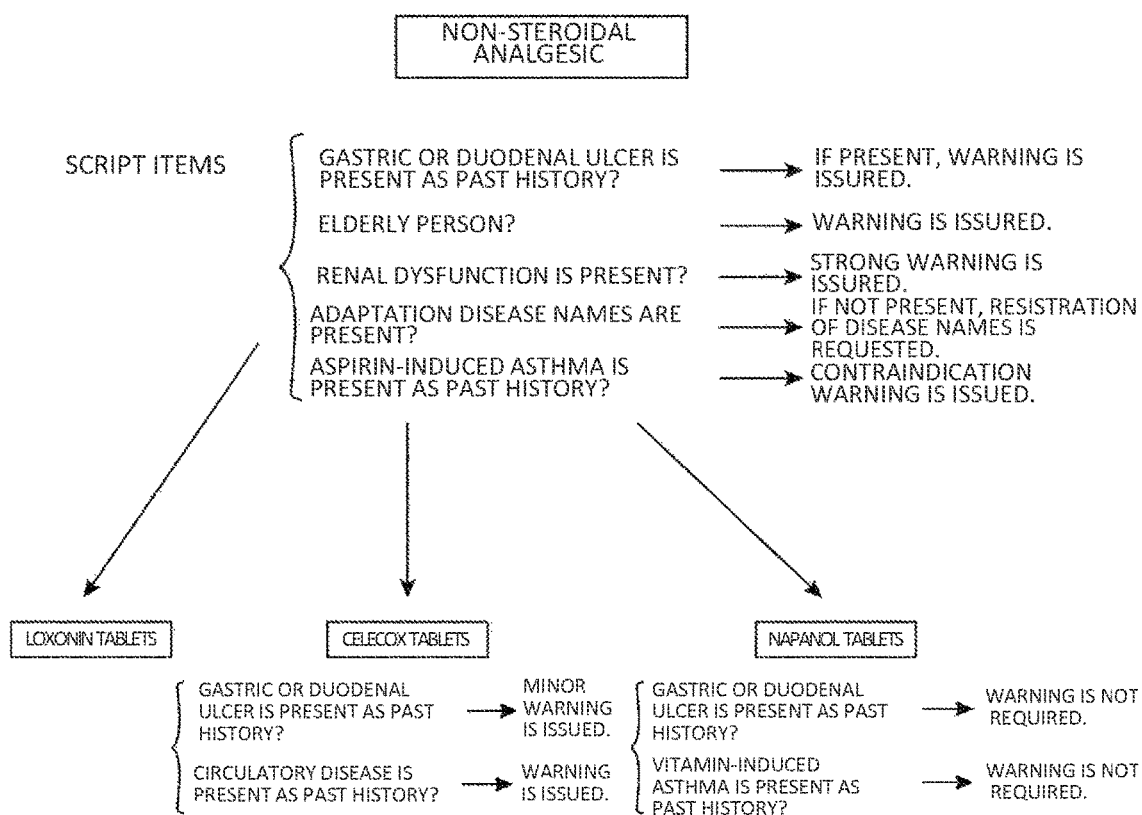
FIG. 6 shows an example in which the common attributes of the term objects are pulled out into a parent term object so that the amount of records is reduced.

FIG. 6 shows an example in which the common attributes of the term objects are pulled out into a parent term project so that the amount of records is reduced and a good view of the logic relationships between the term objects is provided.

First, script items as shown in FIG. 2 are pulled out as common script items of "non-steroidal analgesic." "Loxonin tablets" inherits all the script items of "non-steroidal analgesic."

With respect to "Celecox tablets," a search is performed as to one of the script items, "gastric or duodenal ulcer is present as a past history?". Since Celecox is known to have less adverse effects on ulcer, a minor warning is issued.

Also, since Celecox is known to cause a circulatory complication, a search is performed as to "a circulatory disease is present as a past history?". If present, a warning is issued.

"Napanol tablets" is known to have no adverse effects on gastric or duodenal ulcer or histamine-induced asthma. For this reason, this script item is deleted from the script items inherited from the "non-steroidal analgesic."

Doing so reduces the recording capacity of the term objects managed in the term object management means and clarifies the relationships between the term objects such as the differences therebetween. Also, when a change is made to any description, the resulting description is inherited to the child term objects. This makes maintenance and management easy.

Figures 7, 8:
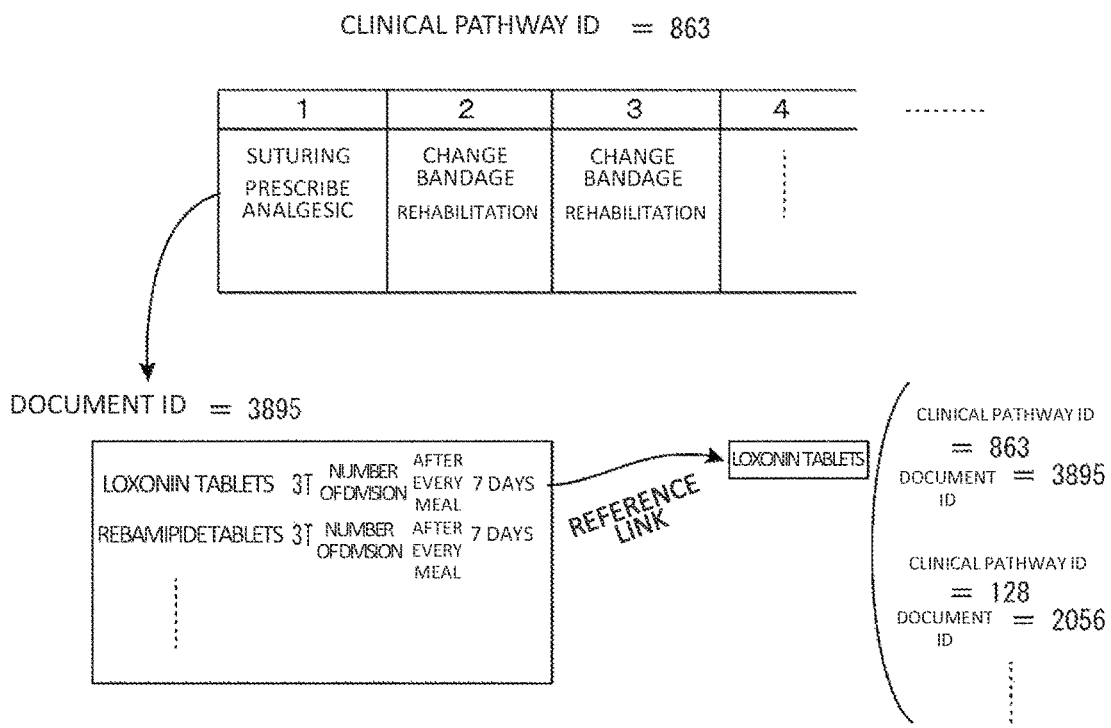
FIG. 7 is a diagram showing that a document requiring a recording capacity for including a term object is converted into plain text so that it is recorded as a weight-reduced document, or conversely, the document converted into the plain text and thus weight-reduced is converted into the document requiring the recording capacity for including the term object.
FIG. 8 is a diagram showing that term objects embedded in clinical pathways using schedule creation means are previously listed in the term object management means and, when changes are made to any term objects, the updated portions are completely listed.

FIG. 7 is a diagram showing that a document requiring a recording capacity for including a term object is converted into plain text so that it is recorded as a weight-reduced document, or conversely, the document converted into the plain text and thus weight-reduced is converted into the document requiring the recording capacity for including the term object.

A term object includes a great amount of additional information to help editing, such as options or script, and therefore would greatly consume the recording capacity of a document if it is recorded as it is.

For this reason, such a document is recorded as plain text when the editing thereof is complete. Thus, the recording capacity can be significantly compressed.

If the document converted into the plain text needs to be reedited, the term object needs to be restored.

The term object is restored by searching for it in the term object management means by a term corresponding to the term object in the document. When converting into plain text, it is useful to put a sign, for example, by underlining the term object or enclosing it in " ".

FIG. 8 is a diagram showing that term objects embedded in clinical pathways using schedule creation means are previously listed in the term object management means and, when changes are made to any term objects, the updated portions are completely listed.

Treatment corresponding to each disease is standardized, and a time schedule for a test or treatment (clinical pathway) is used. A large medical institution has more than 1000 clinical pathways.

When updating test or treatment items in a clinical pathway, it is necessary to visually search for the test or treatment items and to update them one by one and update omission often occurs.

As shown in FIG. 8, the IDs of clinical pathways or documents in which the term objects are used are previously centrally recorded as reference link means in the corresponding term objects in the term object management means. Thus, the test or treatment items to be updated are easily and completely clarified (in-schedule particular term object list display means).

It is more useful to automate updates (in-schedule particular term object update means).

While an embodiment of the present invention has been described, the specific configuration of the present invention is not limited to the embodiment. Design changes and the like in the embodiment are included in the present invention without departing from the spirit and scope of the invention.

For example, while the present invention has been described using the electronic health records in the medical field as an example, a similar mechanism is useful also in areas in which it is appropriate to manage documents for each case using a controlled vocabulary and is included in the present invention. It is also useful to commonly use a part or all of the term object management means with other medical institutions or the like.

The invention claimed is:

1. A document preparation system comprising a processor and a storage device, wherein
   the processor configured to create term objects, the term objects including one or more drugs used as one or more terms in a medical document, further including attributes of the term objects, and further including a script describing checking operation on medical safety to be performed in an electronic health record on the one or more terms when the term objects are selected to make a prescription are integrated, the checking operation includes an operation of searching the electronic medical record for the one or more drugs and warning a prescription doctor on a prescription screen according to a search result, and an operation of searching whether a name of a disease where the prescription of the one or more drugs is approved is registered in the electronic medical record, and displaying a list of disease names when the name is not registered, the processor is configured to record and manage the created term objects, the processor is configured to select a necessary term object from among the term objects managed, the processor is configured to place the selected term object in a document being edited, the processor is configured to organize the term objects into a tree using parent-child relationships in contents between the term objects and to cause child term objects to inherit a script of parent term objects as a script of the child term objects, and the processor is configured to convert the document having the term object placed therein into plain text from which an object element has been removed and to store the plain text in the storage device, said plain text having a reduced recording capacity requirement as compared to the document having the term object.

2. The document creation system of claim 1, wherein the processor is configured to link the term objects placed in the document to at least one of (i) the document or (ii) a case to which the document belongs.

3. The document creation system of claim 1, wherein the processor is configured to record, in the term objects, a freely described comment to be displayed in the document.

4. The document creation system of claim 1, wherein the processor is configured to restore the document converted into the plain text to the document having the term object placed therein.

5. The document creation system of claim 1, wherein the processor is configured to implement, in a schedule in which matters to be executed to achieve a particular purpose are developed on a time axis, the matters to be executed using the term objects.

6. The document creation system of claim 5, wherein the processor is configured to, when changes are made to particular term objects in the schedule, display a list of positions in which the particular term objects are present.

7. The document creation system of claim 6, wherein the processor is configured to update the term objects in the schedule using the changed term objects.

* * * * *